(12) United States Patent
Swenson

(10) Patent No.: US 6,921,388 B2
(45) Date of Patent: Jul. 26, 2005

(54) NEEDLE ASSEMBLY

(76) Inventor: Kirk D. Swenson, 42 Grandview Pl., North Caldwell, NJ (US) 07006

( * ) Notice: Subject to any disclaimer, the term of this patent is extended or adjusted under 35 U.S.C. 154(b) by 0 days.

(21) Appl. No.: 10/287,895

(22) Filed: Nov. 4, 2002

(65) Prior Publication Data
US 2004/0087912 A1 May 6, 2004

(51) Int. Cl.⁷ .......................... A61M 31/00; A61M 5/00; A61M 25/00; A61M 5/32
(52) U.S. Cl. ....................... 604/177; 604/507; 604/110; 604/192; 604/174; 604/263
(58) Field of Search ................................ 604/170–175, 604/110, 192–198, 263, 162, 186, 117, 164, 11, 411, 403, 414, 200, 232, 500–507, 177; 600/573

(56) References Cited

U.S. PATENT DOCUMENTS

| 4,627,843 A | * 12/1986 | Raines ........................ 604/263 |
| 5,312,639 A | 5/1994 | Howard et al. |
| 5,738,665 A | * 4/1998 | Caizza et al. ................ 604/263 |
| 5,746,726 A | * 5/1998 | Sweeney et al. ............ 604/263 |
| 5,951,522 A | * 9/1999 | Rosato et al. ................ 604/177 |
| 5,997,504 A | 12/1999 | Bell |
| 6,261,259 B1 | 7/2001 | Bell |
| 6,436,086 B1 | * 8/2002 | Newby et al. ............... 604/507 |
| 2001/0039401 A1 | * 11/2001 | Ferguson et al. |
| 2002/0072716 A1 | 6/2002 | Barrus et al. |
| 2002/0099342 A1 | 7/2002 | Zurcher |
| 2002/0103463 A1 | 8/2002 | Luther et al. |
| 2004/0049159 A1 | * 3/2004 | Barrus et al. ................ 604/174 |

FOREIGN PATENT DOCUMENTS

| EP | 0 997 159 A1 | 5/2000 |
| EP | 1 256 355 A1 | 11/2002 |
| FR | 2 725 902 | 4/1996 |

* cited by examiner

Primary Examiner—Nicholas D. Lucchesi
Assistant Examiner—Roz Maiorino

(57) ABSTRACT

A needle assembly includes a needle hub with opposite proximal and distal ends and a passage extending between the ends. The needle cannula has a proximal end mounted in the passage of the hub and a distal end aligned at an angle to the proximal end. Wings project transversely from the hub to facilitate a temporary affixation of the needle assembly to a patient. A safety shield is hingedly mounted to the hub and can be rotated from an open position spaced from the needle cannula so that the distal end of the needle cannula can be used to deliver a drug to a patient. The shield also can be rotated to a closed position where the distal end of the needle cannula is safely enclosed within the shield. Locking structure on the shield prevents re-exposure of the needle cannula.

20 Claims, 7 Drawing Sheets

NEEDLE ASSEMBLY

BACKGROUND OF THE INVENTION

1. Field of the Invention

The invention relates to a pivoting shield for a drug administration needle, and particularly for a needle that extends at an angle to the longitudinal axis of the needle hub.

2. Description of the Related Art

Some medical procedures require a liquid drug to be administered over a long period of time. In these situations, medical practitioners are likely to employ an implantable catheter. A typical implantable catheter is identified by the numeral 80 in FIG. 1. Implantable catheter 80 is a generally hollow structure with an inlet end 82, an outlet end 84 and a reservoir 86 therebetween. Catheter 80 may be formed from a plastic, ceramic or non-reactive metallic material. A self-sealing septum 88 extends across the inlet end 82 of implantable catheter 80 and may be formed from a material, such as silicone rubber that can be periodically pierced by a needle, and that will reseal after the needle has been removed.

Catheter 80 is implanted into a patient under local anesthesia by making a small subcutaneous pocket in a selected location on the patient and implanting the catheter 80 into the pocket so that inlet end 82 and septum 88 are slightly below the skin of the patient. Outlet 84 of catheter 80 is positioned deeper in the tissue of the patient and communicates with a site to which the liquid drug is to be administered. Catheter 80 is implanted so that the septum 88 across the inlet ends 82 of the implanted catheter 80 is substantially parallel to the surface of the skin.

The drug typically is administered to the patient by urging a needle cannula through the skin and the small amount of adjacent tissue of the patient that covers the septum 88 of the implanted catheter 80. The needle cannula then is urged through septum 88 and into tubular reservoir 86 of implanted catheter 80.

The needle cannula for delivering the liquid drug to the implanted catheter typically is mounted in a needle hub, which in turn is connected to a length of flexible tubing. The tubing is connected to a reservoir of liquid that contains the prescribed drug. The needle hub typically includes a pair of transverse flexible wings that are substantially coplanar with one another when the wings are in an unbiased condition. However, the wings can be flexed into substantially face-to-face engagement with one another to facilitate manipulation of the needle assembly and specifically for insertion of the needle cannula into the implanted catheter. Once the needle cannula has been positioned properly, the wings are permitted to return to their unbiased condition and are taped into face-to-face engagement with the skin of the patient. The tape prevents the needle assembly from being accidentally dislodged and further prevents painful shifting of the needle cannula that could result if the needle hub or flexible tubing is contacted inadvertently.

Most needle assemblies have the needle cannula aligned along the axis of the needle hub. However, as noted above, implanted catheters generally have their axis aligned perpendicular to the surface of the skin of the patient. Accordingly, the conventional needle assembly cannot be inserted into the above-described implantable catheter 80 and then affixed with tape to the skin of the patient. As a result, implantable catheters often are used with a needle assembly that has a needle cannula aligned perpendicular to the axis of the needle hub. The wings that extend from the needle hub can be taped to the skin of the patient after the needle cannula has been inserted into the implanted catheter.

After a required dose of a liquid drug has been administered to the patient, the needle cannula is withdrawn and discarded. Health care facilities are well aware that accidental sticks with a used needle cannula can transmit disease. Accordingly, most needle assemblies are provided with a shield to prevent accidental sticks. Safety shields for needle cannulas have taken many forms. Some shields are in the form of rigid plastic tubes that are telescoped over the needle cannula prior to use and frictionally retained on the needle hub. These shields are separated from the needle assembly prior to use and then may be telescoped back over the needle cannula after use. Shields of this type are considered undesirable for reshielding because a misalignment between the needle cannula and the shield can cause the accidental stick that the shield is intended to avoid. Other shielding systems include a tubular shield that is mounted over the needle hub proximally of the needle cannula so that the axis of the shield aligns with the axis of the needle and hub. After use, the shield is telescoped along the needle hub and into a position where the shield surrounds the needle cannula. Locking structures on the shield, the hub and/or the needle cannula prevent the shield from being removed completely in a distal direction and further prevent the shield from being returned in a proximal direction that would re-expose the needle. Shields of this type work well and are used widely. Other shields are hingedly mounted to the needle hub and can be rotated from a first position where the shield is spaced from the needle cannula to a second position where the shield surrounds the needle cannula. Locking structure on the shield may engage the needle cannula and/or the needle hub to prevent re-exposure. Hinged needle shields also work very well and are used widely.

The above-described right angle needle for use with an implantable catheter is not well suited to any of the above-described known shields. In particular, shields that require recapping of an exposed needle are as dangerous for a right angle needle as for a conventional needle that is aligned with the axis of the hub. Telescoping needle shields are especially unsuited for right angle needles. The known hinged shields also have not been developed for use with needle assemblies where the needle is aligned at a right angle to the axis of the needle hub.

SUMMARY OF THE INVENTION

The subject invention is directed to a needle assembly having a needle hub with opposite proximal and distal ends and a passage extending between the ends. The proximal end of the hub is configured for connection with a supply of liquid. For example, the proximal end of the hub may be connected to a length of flexible plastic tubing. The end of the flexible plastic tubing opposite the hub may include a fitting that can be connected to a supply of fluid, and particularly a fluid that contains a drug.

The needle assembly may further include a pair of wings projecting transversely from the hub. The wings may be substantially planar in an unbiased condition. However, the wings preferably are configured to be flexed from the unbiased condition and into substantially face-to-face relationship with one another. Thus, the flexed wings can be gripped between a thumb and forefinger to facilitate manipulation of the needle assembly. The wings may be formed unitarily with the hub. Alternatively, the wings may be formed separately and mounted to the hub. The latter alternative enables the hub to be formed from a rigid plastic material and enables the wings to be formed from a flexible material.

The needle assembly further includes a needle cannula having a proximal end, a distal end and a lumen extending the ends. Portions of the needle cannula adjacent the proximal end are affixed in the passage of the needle hub. The extreme distal end of the needle cannula preferably is beveled to a tip that is sufficiently sharp to pierce the skin and adjacent tissue of a patient. The distal end of the needle cannula may define a Huber tip with a non-axial egress aperture. Portions of the needle cannula disposed externally of and distally from the hub are aligned at an angle to portions of the needle cannula fixed in the passage of the hub. The angle preferably is approximately 90°, but may define any selected angle between approximately 60° and 120°. The distal portion of the cannula preferably is aligned at an angle to the plane defined by that portion of the needle assembly resting on the patient's skin, most preferably aligned at an angle to the wings when the wings are in their unbiased condition. Thus, in a preferred embodiment, the distal end of the cannula is substantially perpendicular to the patient's skin in use, most preferably perpendicular to the plane of the unbiased wings.

The needle assembly further includes a shield having opposite proximal and distal ends. Portions of the shield near the proximal end are hinged to the hub. The hinge may comprise a plurality of parts that are engaged with one another, such as a hinge pin and an arcuate bearing. Alternately the hinge may be a unitary connection between the shield and the hub. Portions of the shield between the hinged connection to the hub and the distal end of the shield define a channel with an elongate slot along one longitudinal side of the shield. The slot has a width that exceeds the width of the needle cannula and a length that exceeds the length of portions of the needle cannula that extend beyond the distal end of the hub. Additionally, the slot is disposed to face and receive the needle cannula. Thus the shield can be rotated from an open position were the shield is spaced from the needle cannula to a closed position where the needle cannula is enveloped in the slot of the shield.

The shield may include an actuator that extends proximally or transversely from the hinged connection of the shield with the hub. The actuator preferably is aligned to facilitate application of digital forces to generate a moment that will rotate the shield into the closed position. The actuator can be manipulated by a thumb or forefinger to rotate the shield from the open position to the closed position.

The shield, the hub and/or the needle cannula comprise means for releasably holding the shield in the open position and means for locking the shield in the closed position around the needle cannula. For example, the shield may include at least one resiliently deflectable cannula lock that is cantilevered from a wall of the shield near an open edge of the slot. The cannula lock may project angularly into the slot and may be resiliently deflectable in an inward direction. Thus, the cannula lock will yield as the shield is rotated into the closed position around the needle cannula. Sufficient rotation will enable the cannula lock to pass the cannula. Thus, the cannula lock will resiliently return to an undeflected condition for trapping the needle cannula within the shield and holding the shield in the closed position. Locking means alternatively or additionally may be provided to engage the shield with the hub. For example, the hub may be formed with a pawl-shaped locking structure at or near the distal end of the hub. The shield may include at least one ear for engaging the locking structure on the hub. These engageable components may supplement or replace the cannula lock. Additionally, the engageable structures on the hub and the shield may provide give a tactile and/or audible indication of complete shielding. The primary locking, however, may be achieved with the cannula lock.

The needle assembly is intended primarily for use with an implantable catheter as described above. In particular, the implantable catheter defines a generally tubular reservoir with an entry port at one end. The entry port may be flared outwardly and may be covered by a resealable septum. The catheter is implanted in the patient so that the septum is slightly beneath the skin of the patient and aligned substantially parallel to the skin of the patient. Thus, the needle assembly of the subject invention can be employed by folding the wings into face-to-face relationship with one another and gripping the folded wings between a thumb and forefinger. The beveled distal end of the needle cannula then can be urged through the skin of the patient and through the resealable septum of the implanted catheter. Continued insertion of the needle places the needle within the tubular reservoir defined by the implanted catheter. The needle assembly can be held in place by taping the wings into face-to-face engagement with the skin of the patient. Thus, a liquid drug can be delivered through the flexible plastic tubing, through the needle assembly and into the implanted catheter. This delivery can be continued over an extended period of time.

After a sufficient quantity of the drug has been delivered to the implanted catheter, the tape is removed from the wings and the needle cannula is withdrawn from the patient. Digital pressure then is exerted on the actuator lever to rotate the shield into the closed position. Sufficient rotation will position the needle cannula within the slot of the shield, and the locking structures on the shield, the cannula and/or the hub will engage to prevent re-exposure of the used needle cannula.

DETAILED DESCRIPTION

Figure 1:
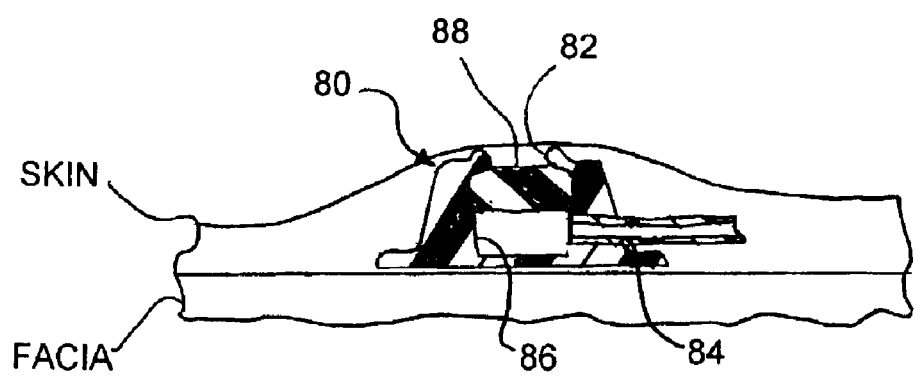
FIG. 1 is cross-sectional view of a known implantable catheter in a patient.
Figure 2:
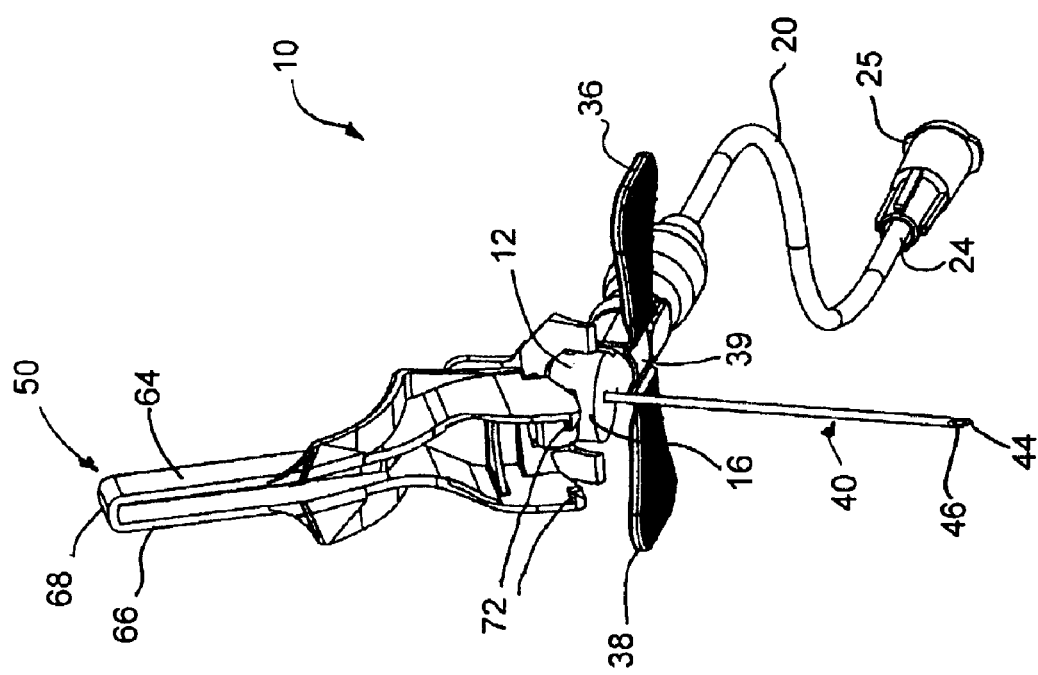
FIG. 2 is a front perspective view of a needle assembly in accordance with the subject invention with the shield in the open position.
Figure 3:
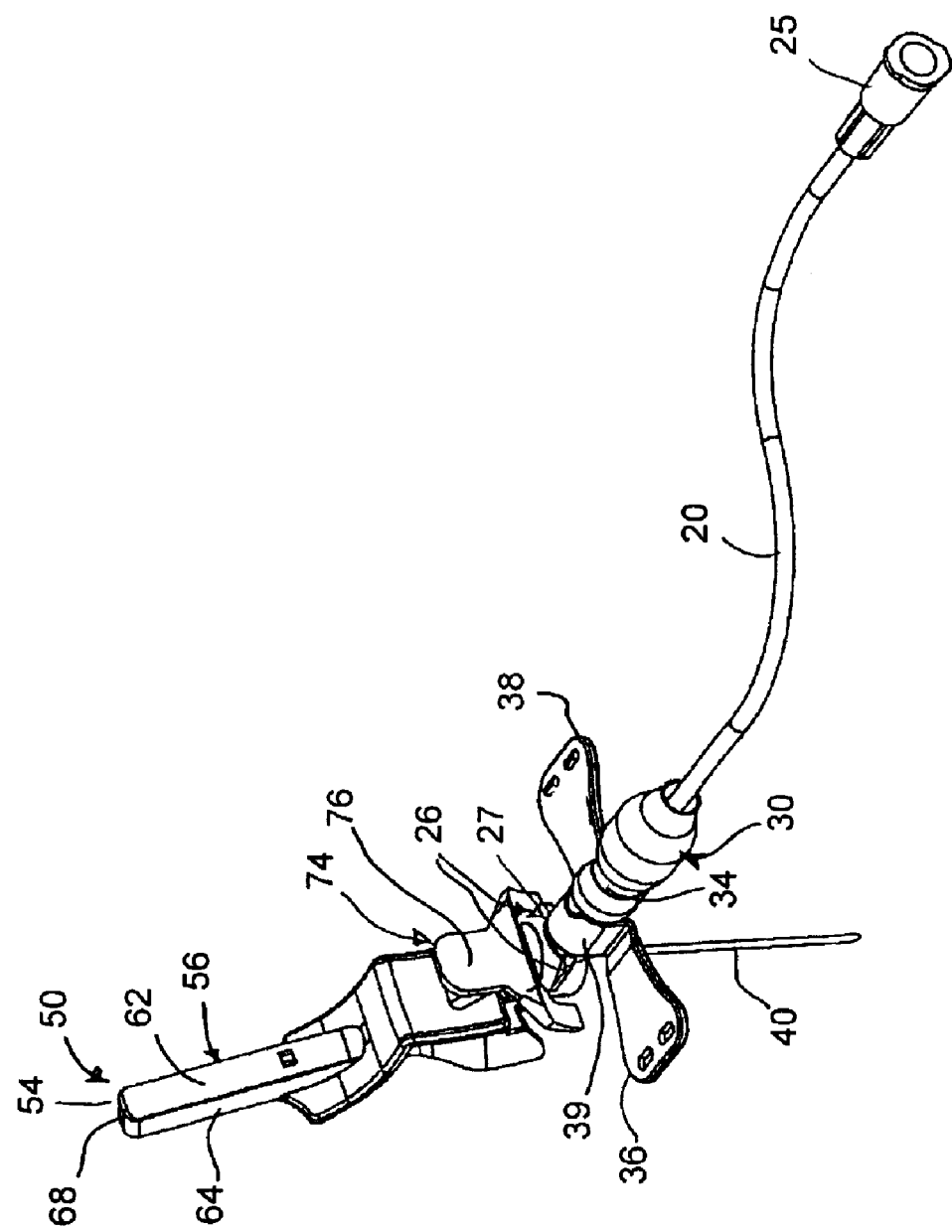
FIG. 3 is a rear perspective view of the needle assembly with the shield in the open position.
Figure 4:
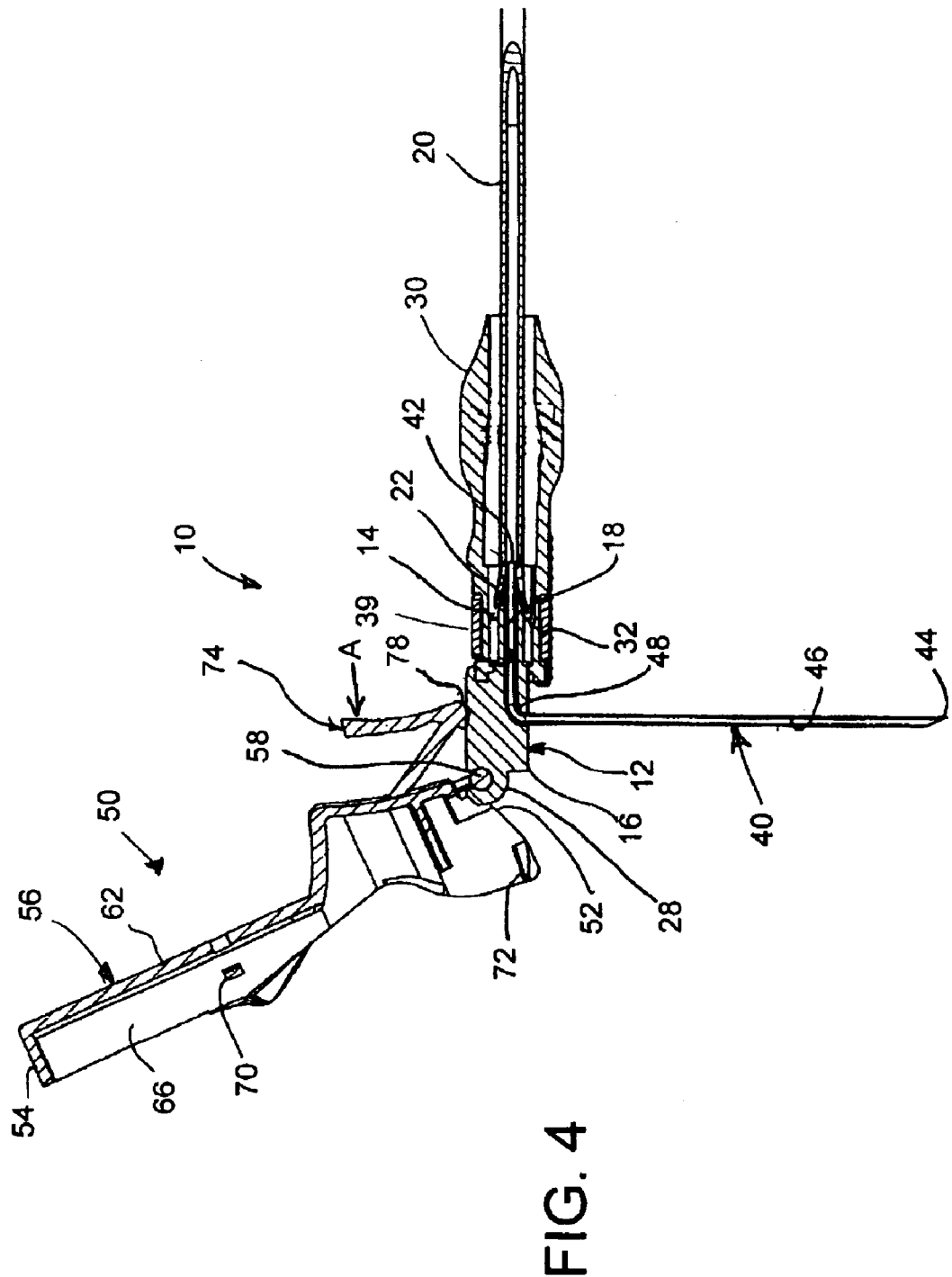
FIG. 4 is a longitudinal cross-sectional view with the shield in the open position.

A needle assembly in accordance with the subject invention is identified generally by the numeral 10 in FIGS. 2–8. Needle assembly 10 includes a hub 12 that is formed unitarily from a rigid thermoplastic material. Hub 12 has a proximal end 14, a distal end 16 and a passage 18 extending between ends 14 and 16, as shown in FIG. 4. External portions of hub 12 adjacent proximal end 14 are dimensioned to engage a length of flexible plastic tubing 20. More particularly, tubing 20 has a distal end 22 that can be telescoped over proximal end 14 of hub 12 and secured in position by adhesive or the like. Tubing 20 further includes a proximal end 24 and a passage extending between the ends. A fitting 25 is secured to proximal end 24 of tubing 20 to enable tubing 20 to be connected to a reservoir of a liquid that contains a drug. Portions of hub 12 between proximal and distal ends 14 and 16 include a pair of locking detents 26 disposed respectively on opposite sides of hub 12. Each locking detent 26 has an upper locking face 27 aligned substantially parallel to portions of passage 18 at proximal end 14 of hub 12. Distal end 16 of hub 12 includes a C-shaped hinge mount 28 that opens transversely on hub 12 at a location distally of locking detents 26.

Needle assembly 10 also includes a generally tubular holder 30 mounted around proximal end 14 of hub 12. Holder 30 may be formed from two longitudinal halves that are bonded or welded together around proximal end 14 of hub 12. The distal end of tubular holder 30 includes a broad annular undercut 32. Intermediate portions of holder 30 forms a cross-sectionally small waist 34 to facilitate digital gripping and manipulation.

Needle assembly 10 further includes first and second wings 36 and 38 that project transversely from portions of tubular holder 30 that are mounted around proximal end of hub 12. Wings 36 and 38 are molded unitarily with a mounting tube 39 and are formed from a resilient flexible material. Mounting tube 39 is dimensioned for frictional engagement over annular undercut 32 of holder 30. In an unbiased condition, wings 36 and 38 are substantially coplanar and substantially tangent to an external face of holder 30. However, wings 36 and 38 can be rotated toward one another and into substantially face-to-face engagement with one another. Thus, wings 36 and 38 can be gripped between a thumb and forefinger for convenient manipulation of needle assembly 10.

Needle assembly 10 further includes a needle cannula 40. Needle cannula 40 has a proximal end 42, a distal end 44 and a lumen 46 extending between the ends. Distal end 44 of needle cannula 40 is beveled to a sharp point that is capable of piercing skin and adjacent tissue. Distal end 44 also could define a Huber tip with a non-axial opening. Portions of needle cannula 40 adjacent proximal end 42 are fixed in passage 18 of needle hub 12 by epoxy or other known bonding techniques. Portions of needle cannula 40 that project distally beyond hub 12 are aligned at an angle of approximately 90° to portions of needle cannula 40 within hub 12. A 90° bend 48 between proximal and distal ends 42 and 40 of needle cannula 40 is embedded in the plastic material of hub 12 for support. In this regard, hub 12 may be insert molded around bend 48 and proximal portions of needle cannula 40 to define a unitary matrix of plastic surrounding and supporting needle cannula 40.

Figure 5:
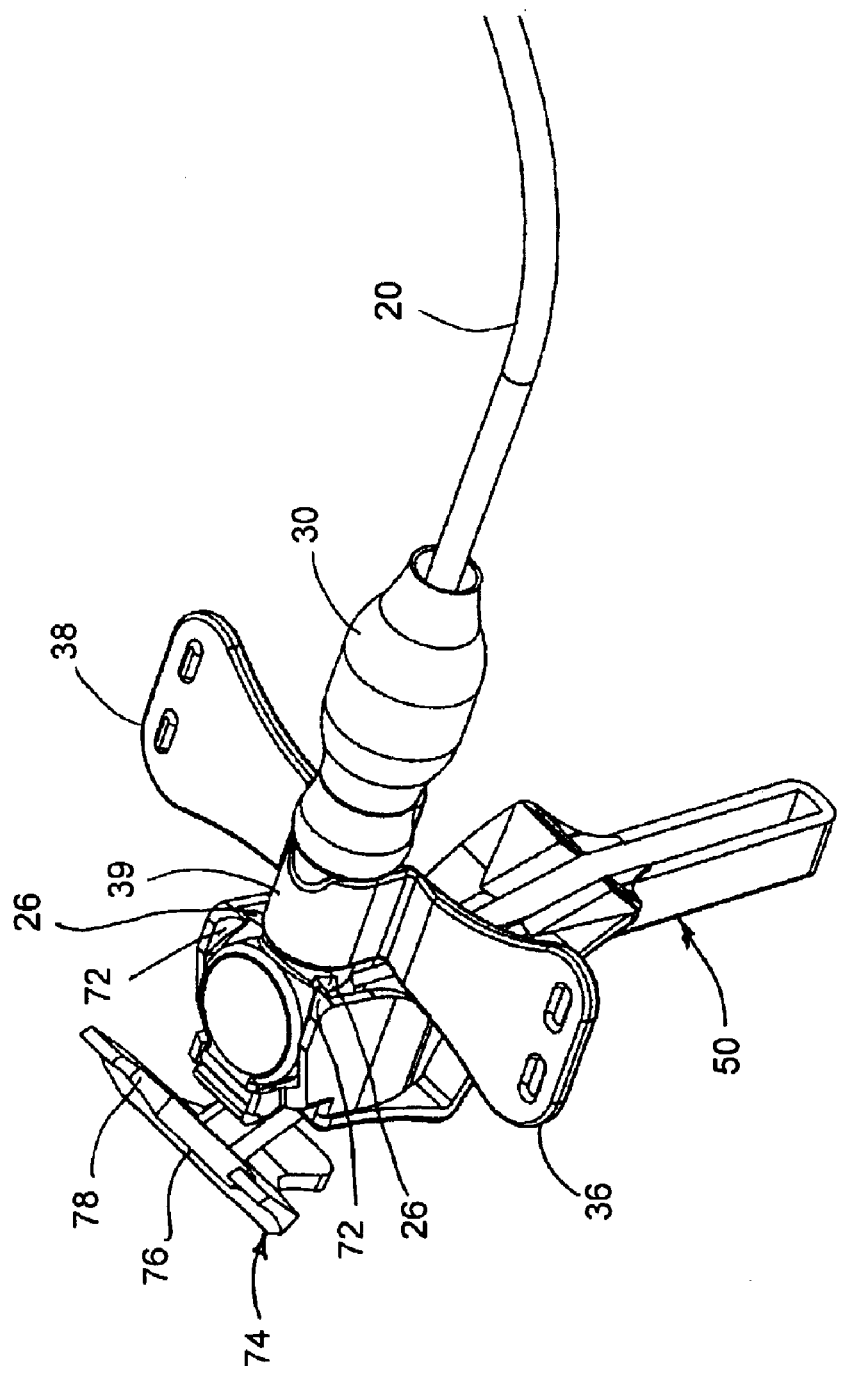
FIG. 5 is a perspective view of the needle assembly with the shield in the closed position.
Figure 6:
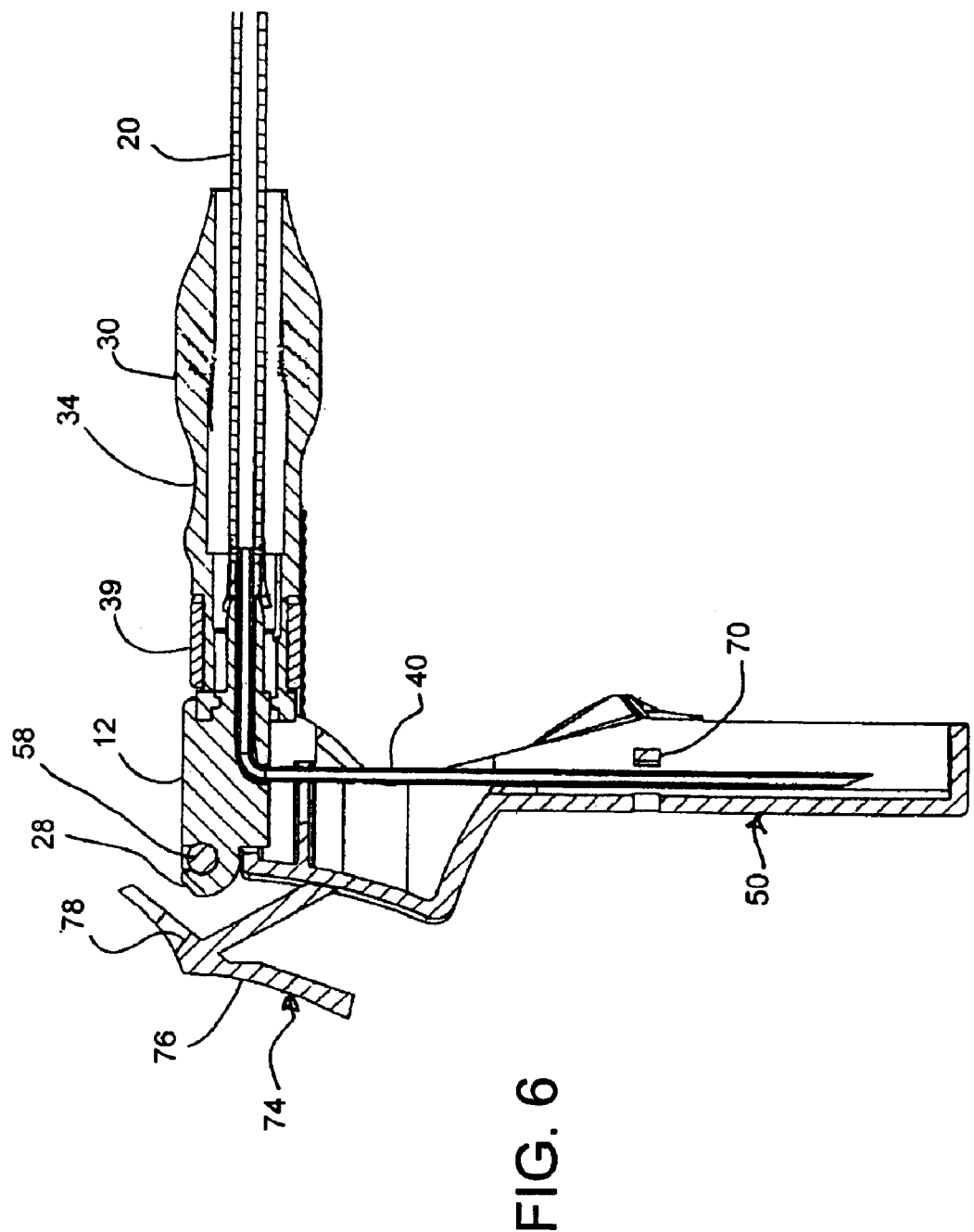
FIG. 6 is a longitudinal cross-sectional view of the needle assembly with the shield in the closed position.

Needle assembly 10 further includes an elongate shield 50 that has a proximal end 52, a distal end 54 and a generally U-shaped channel 56 extending between the ends. Shield 50 preferably is formed from a rigid plastic material that may be the same material as hub 12. However, shield 50 preferably is formed from a material that is distinct and different from the flexible wings 36 and 38. Proximal end 52 of shield 50 includes a hinge pin 58 snapped into rotatable engagement with C-shaped hinge mounts 28 of needle hub 12. The engagement of hinge pin 58 with hinge mounts 28 permits shield 50 to be rotated from an open position, as shown in FIGS. 2–4, to a closed position, as shown in FIGS. 5 and 6. Rotation of shield 50 is about an axis defined by hinge pin 58. The axis of rotation is substantially perpendicular to a plane that passes symmetrically through bent cannula 40. This axis of rotation defined by hinge pin 58 also is substantially parallel to a plane defined by wings 36 and 38 in their substantially coplanar unbiased condition. Other hinged arrangements between shield 50 and hub 12 can be adopted. For example, the C-shaped hinge mounts may be formed on shield 50, and a hinge pin may be formed on hub 12. Still further, a unitary living hinge may be provided between shield 50 and hub 12, as explained below.

Substantially U-shaped channel 56 has a top wall 62 and first and second sidewalls 64 and 66 that extend orthogonally from top wall 62. Sidewalls 64 and 66 are spaced from one another by a distance that exceeds the outside diameter of needle cannula 40. Sidewalls 64 and 66 and top wall 62 are joined by a distal end wall 68. Distal end wall 68 is spaced from hinge pin 58 by a distance that exceed the length of needle cannula 40 that projects from needle hub 12. Thus, when needle shield 50 is rotated from the open position shown in FIGS. 2–4 to the closed position shown in FIGS. 5 and 6, needle cannula 40 is disposed between sidewalls 64 and 66. Shield 50 further includes a cannula lock 70 that projects from a portion of sidewall 66 spaced from the top wall. More particular, cannula lock 70 is aligned at an acute angle toward top wall 62. Cannula lock 70 will engage needle cannula 40 as the shield is rotated into the closed position of FIGS. 5 and 6. As a result, cannula lock 70 will deflect toward sidewall 66 so that needle cannula 40 can enter deeper into the slot defined between sidewalls 64 and 66. Sufficient movement of shield 50 relative to needle cannula 40 will cause needle cannula 40 to pass beyond the free end of cannula lock 70. Hence, cannula lock 70 will return resiliently to an undeflected condition and will trap needle cannula 40 safely within shield 50.

Sidewalls 64 and 66 of shield 50 further include inwardly projecting locking ears 72. Locking ears 72 have locking surfaces 73 that are dimensioned and disposed to engage locking faces 27 of locking detents 26 on hub 12 as shield 50 moves into the closed position. The specific configurations of detents 26 and locking ears 72 can vary depending upon the desired function of the respective structures. For example, locking detents 26 and locking ears 72 can be configured to provide both a tactile and audible indication of complete shielding. With this option, locking of shield 50 in the closed position is achieved by engagement of cannula lock 70 with needle cannula 40. However, locking detents 26 and locking ears 72 can be configured to contribute significantly to the locking of shield 50 in the closed position of FIGS. 5 and 6.

Safety shield 50 further includes an actuator tab 74 that projects from portions of top wall 62 near proximal end 52 of shield 50. In particular, actuator tab 74 defines a generally arcuate actuating surface 76 aligned substantially parallel to top wall 62, substantially perpendicular to the axis of hub 12 when shield 50 is in the open position and substantially perpendicular to the plane of wings 36 and 38 in their unbiased coplanar disposition. Thus, actuating surface 76 is aligned so that a user can apply a moment to shield 50 by application of a force substantially parallel to the plane of wings 36 and 38. Actuator tab 74 enables shield 50 to be manipulated and rotated about hinge mount 28 by exerting digital pressure on actuating surface 76. Additionally actuator tab 74 is disposed distally of wings 36 and 38 when shield 50 is in the open position of FIGS. 2–4. Thus, wings 36 and 38 can be folded into face-to-face engagement when shield 50 is in the open position without interference with actuator tab 74. Furthermore, actuator tab 74 has a bottom edge 18 disposed to engage the outer top surface of hub 12 for preventing shield 50 from rotating in the open direction into a position where manipulation of wings 36 and 38 is impeded.

Needle assembly 10 may further include a package cap (not shown). The packaging cap is a generally tubular member that is formed from rigid plastic material and is configured for mounting over needle cannula 40 prior to use. The packaging cap includes an open proximal end configured for frictional mounting with portions of needle hub 12 at or near distal end 16.

Needle assembly 10 is used by initially rotating wings 36 and 38 into substantially face-to-face engagement with one another and holding the wings between a thumb and forefinger. The packaging cap then is pulled away from wings 36 and 38 with sufficient force to separate the packaging cap from hub 12. Distal end 44 of needle cannula 40 then is urged though the skin of the patient and through septum 84 of implanted catheter 80. Needle assembly 10 is urged sufficiently toward the patient for wings 36 and 38 to lie in face-to-face relationship with the skin. Tape then is applied to secure wings 36 and 38 to the skin of the patient. Needle cannula 40 remains in place for a sufficient dosage of the liquid drug to be delivered through the flexible plastic tubing 20 and into the patient. After a sufficient volume of the drug has been administered in this manner, the tape is removed and wings 36 and 38 are rotated back into face-to-face engagement with one another and are gripped between a thumb and forefinger. Needle assembly 10 then is pulled up and away from the patient so that needle cannula 40 is withdrawn from implanted catheter 80. As needle assembly 10 is being moved away from the patient, safety shield 50 is rotated toward the closed position shown in FIGS. 5 and 6. Rotation of shield 50 is achieved by a combination of gravitational forces and pushing forces on surface 76 of actuating tab 74. The pushing forces on actuating surface 76 may be directed substantially parallel to a plane defined by wings 36 and 38 when wings 36 and 38 are in their unbiased coplanar position. The direction of such an actuating force is identified by arrow A in FIG. 4 and generates a moment for pivoting shield 50. As shield 50 approaches the closed position, digital forces may be redirected to edge 78 to complete rotation of shield 50 to the closed position. Sufficient rotation will permit cannula lock 70 to snap into locked engagement with needle cannula 40. Additionally, locking ears 72 will snap into engagement with locking detents 26. Needle assembly 10 then can be disposed of in a sharps receptacle.

Figure 7:
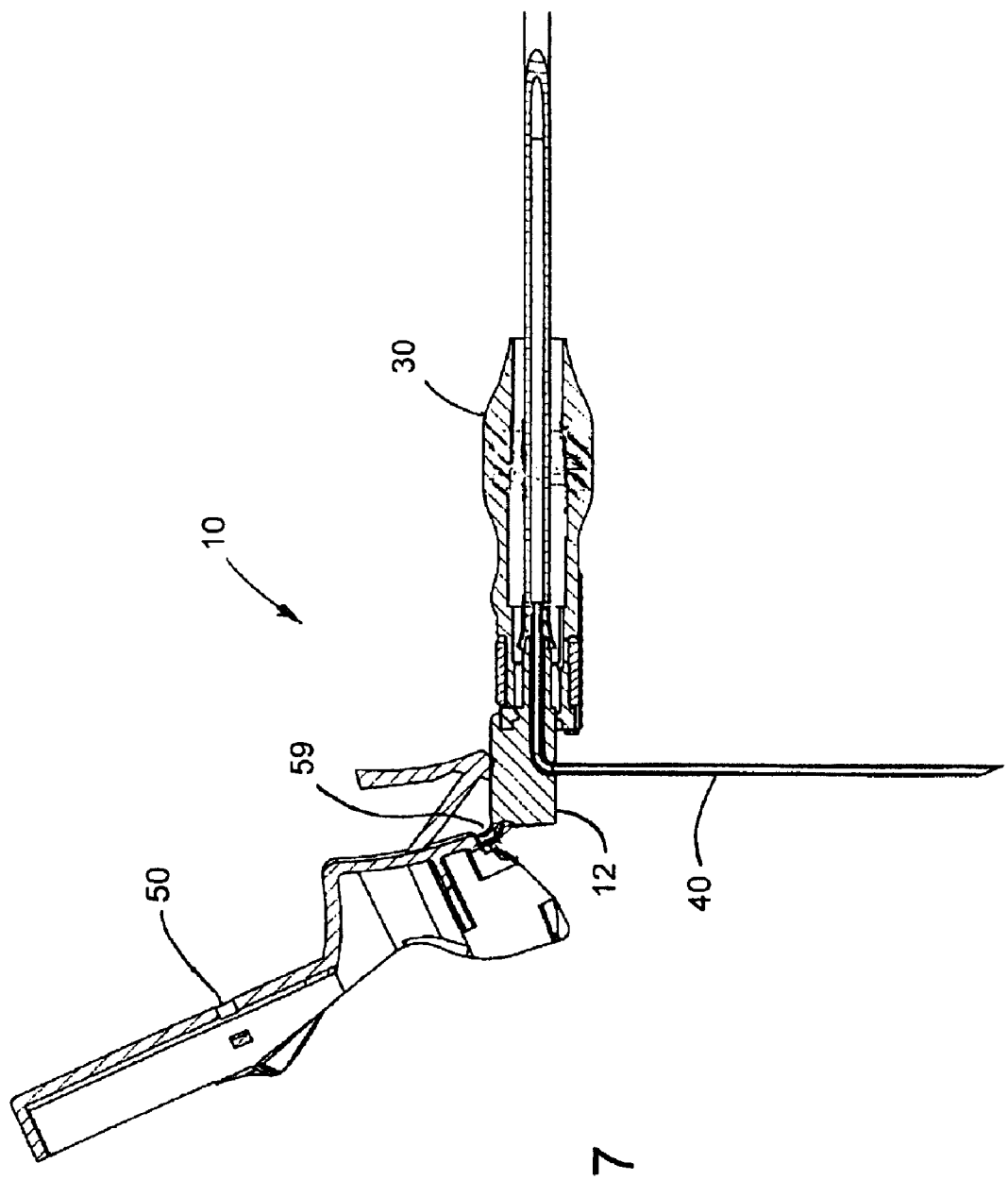
FIG. 7 is a longitudinal cross-sectional view similar to FIG. 4, but showing a shield joined unitarily to the hub by a living hinge.

FIGS. 1–6 show a hub formed with a C-shaped hinge mount 28 and a shield with hinge pin 58 rotatably mounted to mount 28. However, other hinged connections can be provided, including the formation of a living hinge 59 that extends unitarily between shield 50 and hub 12, as shown in FIG. 7. Such a unitary connection can be an over-center hinge that biases shield 50 toward the closed position once an initial rotational movement of shield 50 toward the closed position has commenced.

What is claimed is:

1. A needle assembly comprising:
   needle hub having opposite proximal and distal ends and a passage extending between said ends;
   flexible wings projecting transversely from a portion of said needle assembly in proximity to said hub, said wings, in an unbiased condition, substantially defining a plane;
   a needle cannula having a proximal end and a distal end and a lumen extending between said ends, said needle cannula having a proximal portion adjacent said proximal end of said needle cannula, said proximal portion of said needle cannula being secured in said passage of said needle hub, said needle cannula further having a distal portion adjacent said distal end of said needle cannula and externally of said needle hub, said distal portion of said needle cannula being aligned at an angle to said proximal portion of said needle cannula, said distal end of said needle cannula being on first side of said plane defined by said unbiased wings, said proximal and distal portions of said needle cannula defining a plane aligned substantially normal to said plane defined by said unbiased wings; and
   a safety shield hinged to said hub at a hinge location disposed on a second side of said plane of said unbiased wings and opposite from said first side of said plane, said safety shield being hinged for movement about an axis substantially perpendicular to the plane defined by said proximal and distal portions of said needle cannula from an open position where said distal end of said needle cannula is exposed to a closed position where said distal end of said needle cannula is substantially covered by said safety shield.

2. The needle assembly of claim 1, wherein portions of said needle cannula adjacent said distal end and external of said hub are aligned to said portions of said needle cannula within said hub at an angle of between approximately 60° and 120°.

3. The needle assembly of claim 1, wherein portions of said needle cannula adjacent said distal end and external of said hub are aligned to said portions of said needle cannula within said hub at an angle of substantially 90°.

4. The needle assembly of claim 1, said wings, in an unbiased condition, defining a plane aligned at an angle of between 60° and 120° to portions of said needle cannula adjacent said distal end thereof.

5. The needle assembly of claim 4, wherein the plane defined by said flexible wings in an unbiased condition is substantially orthogonal to said portions of said needle cannula adjacent said distal end thereof.

6. The needle assembly of claim 4, wherein said shield, in said open position, is disposed distally of said wings.

7. The needle assembly of claim 1, wherein one of said needle hub and said needle shield includes a hinge mount, and wherein the other of said needle hub and said needle shield includes a hinge pin hingedly engaged to said hinge mount.

8. The needle assembly of claim 1, wherein said shield is formed unitarily with said needle hub.

9. The needle assembly of claim 8, wherein said unitary connection of said shield to said hub is an over-center hinge for biasing said shield into said closed condition.

10. The needle assembly of claim 1, further comprising at least one resiliently deflectable cannula locking finger formed in said shield for engaging said needle cannula when said shield is in said closed position.

11. The needle assembly of claim 10, further comprising at least one locking detent formed on said hub and at least one locking ear formed on said shield for engaging said locking detent on said hub.

12. The needle assembly of claim 10, wherein the locking detents on the hub include locking surfaces aligned substantially parallel to said portions of said needle cannula adjacent said proximal end.

13. The needle assembly of claim 1, further comprising flexible plastic tubing mounted to said proximal end of said needle hub.

14. The needle assembly of claim 1, wherein said shield has a proximal end, an actuator disposed substantially at said proximal end of said shield and aligned for receiving digital pressure to urge said shield into said closed position.

15. The needle assembly of claim 14, wherein the actuator includes an actuating surface aligned substantially perpendicular to said portions of said needle cannula adjacent said proximal end thereof when said shield is in said open position.

16. The needle assembly of claim 15, wherein said actuator includes a stop edge disposed for contacting said hub and limiting rotation of said hub proximally of said open position.

17. A needle assembly comprising:

a needle hub formed from a thermoplastic material and having a proximal end, a distal end and a passage extending between said ends;

first and second flexible wings mounted in proximity to said needle hub and extending transversely therefrom, said wings, in an unbiased condition, substantially defining a plane having opposite first and second sides;

a needle cannula having a proximal portion, a distal portion and a lumen extending entirely through said needle cannula, said proximal portion being fixed in said passage of said needle hub, said distal portion being aligned to said proximal portion at an angle of between 60°–120° and disposed on said first side of said plane defined by said unbiased wings, said proximal and distal portions of said needle cannula being disposed in a single plane; and a shield hingedly mounted to said hub for rotation about an axis aligned substantially normal to the plane defined by said proximal and distal portions of said needle cannula from a first position where said shield is spaced from said distal portion of said needle cannula to a second position where said shield substantially surrounds said distal portion of said needle cannula, said shield having an actuator disposed on said second side of said plane defined by said unbiased wings when said shield is in first position, said actuator facing towards said proximal portion of said needle cannula for receiving digital pressure to urge said shield from said first position toward second position, said shield comprising means for locking said shield in said second position.

18. The needle assembly of claim 17, wherein the means for locking the shield comprises at least one resiliently deflectable cannula lock unitarily formed with said shield for trapping said needle cannula in said shield when said shield is in said second position.

19. The needle assembly of claim 18, wherein said shield is hingedly mounted to said hub at a location distally of said wings.

20. The needle assembly of claim 1, wherein portions of said needle cannula adjacent said proximal end are disposed on said second side of said plane defined by said wings.

* * * * *

UNITED STATES PATENT AND TRADEMARK OFFICE
CERTIFICATE OF CORRECTION

PATENT NO. : 6,921,388 B2  Page 1 of 1
APPLICATION NO. : 10/287895
DATED : July 26, 2005
INVENTOR(S) : Kirk Swenson It is certified that error appears in the above-identified patent and that said Letters Patent is hereby corrected as shown below:

Title Page, Item [73] add the following Assignee
Becton Dickinson and Company, Franklin Lakes, NJ Signed and Sealed this Fourth Day of July, 2006

JON W. DUDAS
*Director of the United States Patent and Trademark Office*